United States Patent [19]

Kolich et al.

[11] Patent Number: 5,187,135
[45] Date of Patent: Feb. 16, 1993

[54] ASYMMETRIC HYDROGENATION OF AROMATIC-SUBSTITUTED OLEFINS USING ORGANO-COBALT CATALYST

[75] Inventors: Charles H. Kolich; Thanikavelu Manimaran; W. Dirk Klobucar, all of Baton Rouge, La.

[73] Assignee: Ethyl Corporation, Richmond, Va.

[21] Appl. No.: 716,017

[22] Filed: Jun. 17, 1991

[51] Int. Cl.$^5$ .................... B01J 31/00; C07F 15/00; C07F 17/02; C07C 63/04
[52] U.S. Cl. ........................ 502/162; 556/16; 556/21; 562/493; 562/496
[58] Field of Search ............... 562/493, 496; 556/21, 556/16; 502/162

[56] References Cited

U.S. PATENT DOCUMENTS 4,440,936  4/1984  Riley .................................. 562/496

OTHER PUBLICATIONS

Tetrahedron: Asymmetry (2) 1, p. 47 (1991) Alkock et al.

Primary Examiner—Paul J. Killos
Assistant Examiner—Joseph M. Conrad
Attorney, Agent, or Firm—Richard J. Hammond

[57] ABSTRACT

A process for the asymmetric reduction of carboxylic acids of the formula

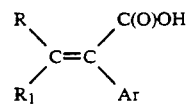

or the amine salts thereof, where R and $R_1$ are the same or different and are hydrogen, alkyl, cycloalkyl or haloalkyl and Ar is aryl or substituted aryl is disclosed.

18 Claims, No Drawings

ASYMMETRIC HYDROGENATION OF AROMATIC-SUBSTITUTED OLEFINS USING ORGANO-COBALT CATALYST

FIELD OF THE INVENTION

This invention relates to a process for the catalytic reduction of aromatic-substituted olefins. More specifically, this invention relates to a process for asymmetrically, catalytically reducing aromatic-substituted olefins using a mixture of an organocobalt compound and an optically active organophosphorous compound.

BACKGROUND OF THE INVENTION

Enantioselective catalysis using chiral metal complexes provides one of the most general and flexible methods for achieving asymmetric organic reactions. Metallic elements possess a variety of catalytic activities, and permutations of organic ligands or other auxiliary groups directing the steric course of the reaction are practically unlimited. Efficient ligands must be endowed with, for example, suitable functionality, appropriate chirality, a structure capable of differentiating space either electronically or sterically and skeletal rigidity or flexibility.

Among the asymmetric organic reactions catalyzed by chiral transition metal complexes, asymmetric hydrogenation has been one of the best studied, due in large part to the fact that it is the basis for the first commercialized catalytic asymmetric process. See, for example, ApSimon, et al., *Tetrahedron*, 1986, 42, 5157.

Some of the more interesting of the asymmetric hydrogenation catalysts are those derived from BINAP [2,2'-bis(diphenylphosphino)-1,1'-binaphthyl]. See, for example, U.S. Pat. Nos.: 4,691,037; 4,739,084; 4,739,085; 4,764,629; 4,994,607; and 4,766,227. Unlike the more classical models of chiral (asymmetric) molecules, chirality in the case of the BINAP compounds arises from the restricted rotation about the single bond joining the naphthalene rings. Isomers arising from this type of asymmetry are termed atropisomers.

BINAP-based Ru(II) and Rh(I) complexes induce high enantioselectivity in catalytic reactions. See Noyori and Takaya, *Acc. Chem. Res.*, 1990, 23, 345.

The BINAP ruthenium complexes are dramatically different than the rhodium ones. They have been used to catalyze a variety of asymmetric hydrogenations, including the hydrogenation of enamides and alkyl and aryl-substituted acrylic acids. See Noyori, et al., *Modern Synthetic Methods*, 1989, 5, 115, incorporated herein by reference. Unlike the rhodium catalyzed reductions, ruthenium(II) carboxylate complexes possessing the BINAP ligand are efficient catalysts for the enantioselective hydrogenation of $\alpha,\beta$-unsaturated carboxylic acids. According to Ohta, et al, *J. Org. Chem*, 52, 3174 (1982), the carboxyl moiety of the substrate, and not other oxygen containing groups, is responsible for the stereoselective reaction. Asymmetric reductions of noncarboxyl-containing substrates by ruthenium complexes are inefficient.

While the chiral phosphine complexes of rhodium and ruthenium are well known to catalyze asymmetric reactions, cobalt has not been established as a metal capable of forming complexes that promote such enantioselective transformations. The general availability and lower cost of cobalt relative to rhodium and ruthenium provide an obvious commercial advantage for cobalt complexes that show reasonable activity as catalysts for asymmetric syntheses.

SUMMARY OF THE INVENTION

The present invention involves a novel method for the use of organocobalt compounds which, when admixed in an appropriate solvent with ligands having optical activity, can be used as in situ catalyst to effect the asymmetric reduction of certain unsaturated organic compounds.

DESCRIPTION OF THE PREFERRED EMBODIMENTS

In the present specification, alkyl means straight or branched chain alkyl having 1 to 20 carbon atoms and includes, for example, methyl, ethyl, propyl, isopropyl, butyl, isobutyl, secondary butyl, tertiary butyl, pentyl, isopentyl, neopentyl, hexyl, heptyl, octyl, 2-ethylhexyl, 1,1,3,3-tetramethylbutyl, nonyl, decyl, dodecyl, tetradecyl, hexadecyl, octadecyl, and eicosyl.

Cycloalkyl means cyclic alkyl having 3 to 7 carbon atoms and includes cyclopropyl, cyclobutyl, cyclopentyl, cyclohexyl and cycloheptyl.

Substituted aryl means phenyl or naphthyl substituted by at least one substituent selected from the group consisting of halogen (chlorine, bromine, fluorine or iodine), amino, nitro, hydroxy, alkyl, alkoxy, which means straight or branched chain alkoxy having 1 to 10 carbon atoms, and includes, for example, methoxy, ethoxy, propoxy, isopropoxy, butoxy, isobutoxy, secondary butoxy, tertiary butoxy, pentyloxy, isopentyloxy, hexyloxy, heptyloxy, octyloxy, nonyloxy and decyloxy, haloalkyl which means straight or alkyl having 1 to 8 carbon atoms which is substituted by at least one halogen, and includes, for example, chloromethyl, bromomethyl, fluoromethyl, iodomethyl, 2-chloroethyl, 2-bromoethyl, 2-fluoroethyl, 3-chloropropyl, 3-bromopropyl, 3-fluoropropyl, 4-chlorobutyl, 4-fluorobutyl, dichloromethyl, dibromomethyl, difluoromethyl, diiodomethyl, 2,2-dichloroethyl, 2,2-dibromoethyl, 2,2-difluoroethyl, 3,3-dichloropropyl, 3,3-difluoropropyl, 4,4-dichlorobutyl, 4,4-difluorobutyl, trichloromethyl, trifluoromethyl, 2,2,2-trifluoroethyl, 2,3,3-trifluoropropyl, 1,1,2,2-tetrafluoroethyl and 2,2,3,3-tetrafluoropropyl.

Haloalkyl means straight or branched chain alkyl having 1 to 10 carbon atoms which is substituted by at least one halogen as mentioned above.

Phenylalkyl means that the alkyl moiety is straight or branched chain alkyl having 1 to 8 carbon atoms and includes, for example, benzyl, 2-phenylethyl, 1-phenylethyl, 3-phenylpropyl, 4-phenylbutyl, 5-phenylpentyl, 6-phenylhexyl and 8-phenyloctyl.

Substituted phenylalkyl means above-mentioned phenylalkyl which is substituted by at least one substituent selected from the group consisting of halogen, amino, nitro, hydroxy, alkyl, alkoxy and haloalkyl on the phenyl nucleus.

Chiral phosphine compound means an optically active alkyl or aryl substituted trivalent phosphorus compound. Examples of such compounds are:

1,2-ethanediyl-bis(o-methoxyphenyl)phenylphosphine (DIPAMP);

N,N'-bis($\alpha$-methylbenzyl)-N,N'-bis(diphenylphosphine) ethylenediamine (PNNP);

2,3-bis(diphenylphosphino)butane (CHIRAPHOS);

1,2-bis(diphenylphosphino)propane (PROPHOS);

2,3-O-isopropylidene-2,3-dihydroxy-1,4-bis(diphenyl-phosphino)butane (DIOP);

2,4-t-butyl 4-(diphenylphosphino)-2-(diphenylphos-phinomethyl)-1-pyrrolidine-carboxylate (BPPM);

2,4-bis(diphenylphosphine)pentane (SKEWPHOS);

2,5-bis(diphenylphosphino)hexane (BDPH);

1,2-bis(diphenylphosphino-1-phenylethane (PHEN-PHOS):

1,2-bis(diphenylphosphino)-1-cyclohexylethane (CYC-PHOS);

α-[1,2-bis(diphenylphosphino)ferrocenyl]-ethyldime-thylamine (BPPFA); and trans-4,5-bis[(5H-dibenzophospholyl)methyl]-2,2-dimethyl-1,3-dioxolane (DIPHOL).

A detailed description of suitable phosphines for the present invention is disclosed in "Asymmetric Synthesis", Vol. 5, Ed. by James D. Morrison, Academic Press, Orlando (1985), incorporated herein by reference.

The enantioselective preparations of the present invention are carried out optionally using amine salts of α-aryl olefinic carboxylic acids. When amine salts are used, they are derived from a wide variety of primary, secondary or tertiary hydrocarbyl amines. They include the aromatic amines, aliphatic amines, mixed aromatic-/aliphatic amines, as well as heterocyclic and cycloaliphatic amines. Such hydrocarbyl amino compounds are illustrated by methylbenzylamine, ethyldiisopropylamine, N-methylpiperdine, triethylamine, pyrrole, etc. They react readily with the carboxylic acid function of the α-aryl olefinic carboxylic acid to produce amine salts, usually by preparing a solution of equimolar amounts of the two reactants. The resulting amine salts, generated in situ or preformed, are used in the subsequent step of the process of this invention.

The carboxylic acids have the formula

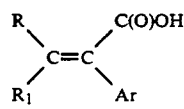

where R and $R_1$ are the same or different and are hydrogen, alkyl, cycloalkyl, or haloalkyl and Ar is aryl or substituted aryl. Preferably R and $R_1$ are the same or different and are hydrogen or alkyl. The amine salts are also useful in the process of the present invention. Most preferred in the above carboxylic acid is where R and $R_1$ are the same and are hydrogen or methyl. They are reduced (hydrogenated) asymmetrically by a catalytic process employing a mixture of (i) a cobalt material and (ii) an optically active ligand in an appropriate solvent where the ligand is

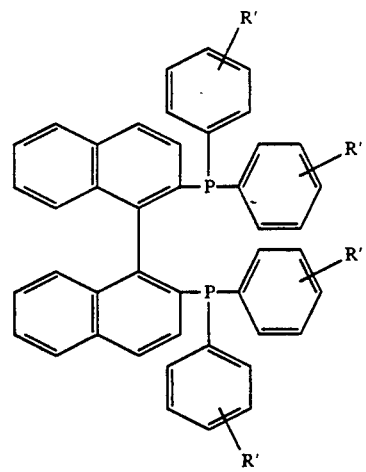

where R' is hydrogen (BINAP), alkyl, haloalkyl, aryl or substituted aryl. It is neither necessary nor economically desirable to isolate the chiral metal catalyst that may be formed in this mixture prior to hydrogenation of the substrate.

Cobalt-containing materials of use in this invention may be any of a wide variety of forms and include, for example, the halides such as cobalt(II) bromide, cobalt(III) bromide, cobalt(II) acetate, cobalt(III) acetate, cobalt(II) chloride, or cobalt(II) chloride and the mixed halide-chelate complexes such as (cycloocta-1,5-diene)-cobalt(II) chloride polymer, i.e., the chelate complex salts, or (cycloocta-1,5-diene)cobalt(II), chelate complexes such as cobalt(II) (2,4-pentanedionate) or cobalt(III) (2,4-pentanedionate). The hydrated forms of the above compounds are also useful herein.

The preferred cobalt compounds of use in the process of the present invention are the chelate complexes of the formula

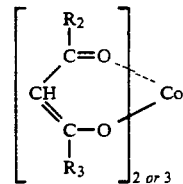

where $R_2$ and $R_3$ are the same or different and are alkyl, aryl, haloalkyl, phenylalkyl or substituted phenylalkyl.

In the preferred cobalt compound, it is most preferred that $R_2$ and $R_3$ are the same and are alkyl of 1 to 12 carbon atoms having a linear or branched chain. Particularly preferred are where $R_2$ and $R_3$ are the same and are linear or branched $C_1$ to $C_6$ alkyl group. Illustrative alkyl groups most preferably employed as $R_2$ and $R_3$ are methyl, ethyl, propyl, isopropyl, butyl, isobutyl, secondary butyl, tertiary butyl, pentyl, isopentyl, neopentyl, trifluoromethyl and the like.

The chiral organophosphorous compound admixed with the cobalt compound is preferably one where all R' are the same and are hydrogen or $C_1$ to $C_6$ linear or branched alkyl. Most preferably all R' are the same and are hydrogen, methyl, ethyl, propyl or isopropyl.

The asymmetric catalytic hydrogenations utilizing the catalyst mixture of (i) and (ii) above is mixed with a solution of an α-aryl olefinic carboxylic acid or its amine salt, typically in a molar ratio of (i):(ii) of 10:1 to 1:10, preferably 8:1 to 1:8, most preferably 1:1.

The molar ratio of (i) to the olefinic acid or its amine salt is between about 1 to 20 to about 1 to 20,000, preferably about 1 to 100 to about 1 to 10,000, most preferably about 1 to 5,000 to about 1 to 10,000.

The combination of the catalyst mixture, the olefinic carboxylic acid (or amine salt of such acid) and suitable organic solvent, provide a system suitable for hydrogenation at elevated hydrogen pressure, i.e., pressures above about 75 psig.

To achieve enantioselective hydrogenation of a free α-olefinic carboxylic acid, a mixture of (i) and (ii) in the hydrogenation solvent must be given time (typically 1 to 5 hours) to become activated, either with or without hydrogen pressure at room temperature or at elevated temperature, before the substrate is introduced.

The chemical reactions described above are generally disclosed in terms of their broadest application to the preparation of the compounds of this invention. Occasionally, the reactions may not be applicable as described to each compound included within the disclosed scope. The compounds for which this occurs will be readily recognized by those skilled in the art. In all such cases, either the reactions can be successfully performed by conventional modifications known to those skilled in the art, e.g., by appropriate protection of interfering groups, by changing to alternative conventional reagents, by routine modification of reaction conditions, and the like, or other reactions disclosed herein or otherwise conventional, will be applicable to the preparation of the corresponding compounds of this invention. In all preparative methods, all starting materials are known or readily prepared from known starting materials.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

EXAMPLES

General

All solvents used in the hydrogenation were reagent grade and were sparged with nitrogen for at least 2 hours to remove oxygen. The S-BINAP, cobalt(II) (2,4-pentanedionate) and cobalt(III) (2,4-pentanedionate) used were commercially available materials. Conversions were determined by GC (area %). Optical purities were determined by HPLC using a chiral column. The hydrogenation reactor used was constructed of Monel 400.

EXAMPLE 1

To a 100 ml pressure reactor in a nitrogen-filled glove box was added 14 mg (0.054 mmol) of cobalt(II) (2,4-pentanedionate) [Co(acac)$_2$], 33 mg (0.053 mmol) of S-BINAP and 30 ml methanol. The reactor was purged with hydrogen and stirred (300 rpm) for 4 hours at 24° C. with 1000 psi hydrogen. The reactor was vented, and a solution of 336 mg (1.65 mmol) of 2-(4-isobutylphenyl)acrylic acid (UA) in 10 ml of methanol was added to the vessel. The reactor was purged with hydrogen (3×300 psi) and stirred 47 hours at 23° C. with 1000 psi hydrogen. GC showed 5% conversion of UA to ibuprofen. Tetrahydrofuran (inhibited, 25 ml) was added to the mixture. The reactor was purged with hydrogen (3×300 psi) and stirred at 60° C. for 19 hours with 1000 psi hydrogen. The conversion of UA to ibuprofen was 16% and the optical purity of the ibuprofen was 98% (S).

EXAMPLE 2

To a 100 ml pressure reactor in a nitrogen-filled glove box was added 16 mg (0.062 mmol) of Co(acac)$_2$, 38 mg (0.061 mmol) of S-BINAP and 30 ml of a 1:1 mixture of methanol and tetrahydrofuran. The reactor was purged with hydrogen and stirred (300 rpm) at 24° C. with 1000 psi hydrogen for 19 hours. The vessel was vented, and 301 mg (1.48 mmol) of UA in 10 ml of a 1:1 mixture of tetrahydrofuran and methanol was added to the reactor in a nitrogen-filled glove box. The reactor was purged with hydrogen and stirred at 24° C. for 22 hours with 1000 psi hydrogen. GC showed no ibuprofen had formed. The reaction was continued at 60° C. for 51 hours. GC showed 8% conversion to ibuprofen of 98% (S) optical purity. After an additional 24 hours at 100° C., GC showed that the conversion of UA to ibuprofen was 8% and the optical purity was 84% (S).

EXAMPLE 3

To a 100 ml pressure reactor in a nitrogen-filled glove box was added 17 mg (0.066 mmol) of Co(acac)$_2$, 50 mg (0.080 mmol) of S-BINAP and 30 ml of methanol. The reactor was purged with hydrogen and stirred for 19 hours at 21° C. with 1000 psi hydrogen. The reactor was vented, and a solution of 396 mg (1.94 mmol) of UA in 10 ml of methanol was added. The reactor was purged with hydrogen and stirred at 25° C. for 21 hours with 1000 psi hydrogen. GC showed that no ibuprofen had formed. The reactor was warmed to 60° C. and stirred at 60° C. for 24 hours with 1000 psi hydrogen. GC showed 9% conversion to ibuprofen of 98% (S) optical purity. The reaction was continued for 24 hours at 100° C. with 1000 psi hydrogen. The conversion of UA to ibuprofen was 10% and the optical purity was 90% (S).

EXAMPLE 4

To a 100 ml pressure reactor in a nitrogen-filled glove box was added 24 mg (0.067 mmol) of cobalt(III) (2,4-pentanedionate) [Co(acac)$_3$], 45 mg (0.072 mmol) of S-BINAP and 30 ml of methanol. The reactor was purged with hydrogen and stirred (300 rpm) for 4.3 hours at 25° C. with 1000 psi hydrogen. The reactor was vented, and a solution of 366 mg (1.79 mmol) UA in 10 ml of methanol was added in a nitrogen-filled glove box. The reactor was purged with hydrogen and stirred 17 hours at 24° C. with 1000 psi hydrogen. GC showed that no ibuprofen had formed. The reaction was continued at 60° C. with 1000 psi hydrogen. GC analysis of a sample taken after 5.3 hours at 60° C. showed 25% conversion to ibuprofen. After 23 hours at 60° C., GC showed 43% conversion to ibuprofen. The reaction was stopped after 47 hours at 60° C. where GC showed 45% conversion to ibuprofen, and HPLC indicated an optical purity of 76% (S).

TABLE

| | | | | IN SITU HYDROGENATION RESULTS | | | |
| | | | | (900-1000 psi $H_2$ IN METHANOL) | | | |
| EXAMPLE | SUBSTRATE | METAL COMPLEX | PHOSPHINE LIGAND | SOLVENT | TEMP/TIME (°C./hr) | CONVERSION (GC Area %) | % ee |
|---|---|---|---|---|---|---|---|
| 1 | UA | Co(acac)$_2$ | S-BINAP | MeOH/THF (1.6:1) | 23/47 | 5 | |
| | | | | | 60/19 | 16 | 98 (S) |
| 2 | UA | Co(acac)$_2$ | S-BINAP | MeOH/THF (1:1) | 24/22 | 0 | |
| | | | | | 60/51 | 8 | 96 (S) |
| | | | | | 100/66 | 8 | 84 (S) |
| 3 | UA | Co(acac)$_2$ | S-BINAP | MeOH | 25/21 | 0 | |
| | | | | | 60/24 | 9 | 99 (S) |
| | | | | | 100/24 | 10 | 90 (S) |
| 4 | UA | Co(acac)$_3$ | S-BINAP | MeOH | 24/17 | 0 | |
| | | | | | 60/5.3 | 25 | |
| | | | | | 60/23 | 43 | |
| | | | | | 60/47 | 45 | 76 (S) |

We claim:

1. A process for preparing optically active α-aryl aliphatic carboxylic acids which comprises catalytically, asymmetrically hydrogenating a carboxylic acid of the formula

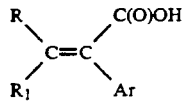

or the amine salt thereof, where R and $R_1$ are the same or different and are hydrogen, alkyl, cycloalkyl, or haloalkyl; and Ar is aryl or substituted aryl; by utilizing a catalytically effective amount of a mixture of (i) a cobalt compound of the formula

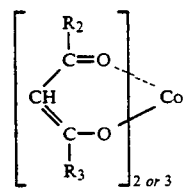

where $R_2$ and $R_3$ are the same or different and are alkyl, haloalkyl, aryl, substituted aryl, phenylalkyl or substituted phenylalkyl; and (ii) a chiral phosphine compound.

2. The process according to claim 1 wherein said cobalt compound is a halide, a mixed halide-chelate complex or a chelate complex.

3. The process of claim 1 wherein R and $R_1$ are the same or different and are hydrogen or alkyl.

4. The process according to claim 3 wherein R and $R_1$ are hydrogen.

5. The process according to claim 1 wherein Ar is phenyl or naphthyl substituted with alkyl or alkoxy.

6. The process according to claim 5 wherein Ar is phenyl substituted with methyl, ethyl, n-propyl or isobutyl.

7. The process according to claim 1 wherein $R_2$ and $R_3$ are the same and are alkyl.

8. The process according to claim 7 wherein $R_2$ and $R_3$ are methyl.

9. A process for preparing optically active α-aryl aliphatic carboxylic acids which comprises catalytically, asymmetrically hydrogenating a carboxylic acid of the formula

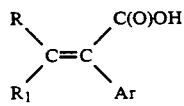

or the amine salt thereof, where R and $R_1$ are the same or different and are hydrogen, alkyl, cycloalkyl, or haloalkyl; and Ar is aryl or substituted aryl; by utilizing a mixture of (i) a cobalt compound of the formula

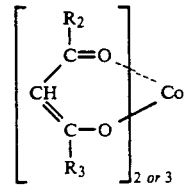

where $R_2$ and $R_3$ are the same or different and are alkyl, phenylalkyl or substituted phenylalkyl; and (ii) an optically active ligand where the ligand is

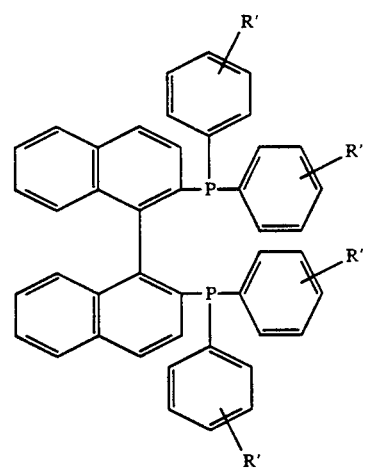

where R' is hydrogen, alkyl, haloalkyl, aryl or substituted aryl.

10. The process according to claim 9 wherein said cobalt compound is a halide, a mixed halide-chelate complex or a chelate complex.

11. The process of claim 9 wherein R and $R_1$ are the same or different and are hydrogen or alkyl.

12. The process according to claim 11 wherein R and $R_1$ are hydrogen.

13. The process according to claim 9 wherein Ar is phenyl or naphthyl substituted with alkyl or alkoxy.

14. The process according to claim 13 wherein Ar is phenyl substituted with methyl, ethyl, n-propyl or isobutyl.

15. The process according to claim 9 wherein $R_2$ and $R_3$ are the same and are alkyl.

16. The process according to claim 15 wherein $R_2$ and $R_3$ are methyl.

17. An asymmetric hydrogenation catalyst composition comprising a mixture of BINAP and a cobalt compound represented by the formula

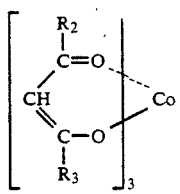

where $R_2$ and $R_3$ are the same and are methyl.

18. A process for preparing S-ibuprofen which comprises catalytically, asymmetrically hydrogenating 2-(4-isobutylphenyl)acrylic acid by utilizing a mixture of

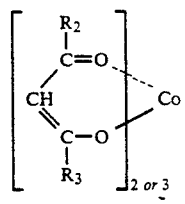

and an optically active BINAP, where $R_2$ and $R_3$ are the same or different and are alkyl and BINAP is

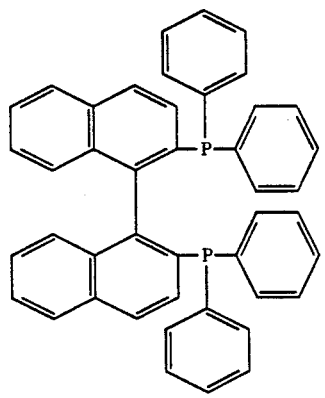

* * * * *